United States Patent
Bragulla et al.

(10) Patent No.: US 6,191,092 B1
(45) Date of Patent: Feb. 20, 2001

(54) LIQUID ENZYME PREPARATION AND THE USE THEREOF

(75) Inventors: Siegfried Bragulla, Monheim; Andreas Potthoff, Duesseldorf; Wilfried Serve, Leverkusen, all of (DE)

(73) Assignee: Henkel Kommanditgesellschaft auf Aktien, Duesseldorf (DE)

( * ) Notice: Under 35 U.S.C. 154(b), the term of this patent shall be extended for 0 days.

(21) Appl. No.: 09/403,540

(22) PCT Filed: Apr. 15, 1998

(86) PCT No.: PCT/EP98/02200

§ 371 Date: Oct. 22, 1999

§ 102(e) Date: Oct. 22, 1999

(87) PCT Pub. No.: WO98/47993

PCT Pub. Date: Oct. 29, 1998

(30) Foreign Application Priority Data

Apr. 24, 1997 (DE) .............................................. 197 17 329

(51) Int. Cl.[7] .............................. C11D 3/386; C11D 3/43; C11D 3/44

(52) U.S. Cl. ................ 510/392; 510/530; 510/226; 510/320; 510/321; 510/319; 510/382; 510/383; 510/337; 510/339; 510/498; 510/500

(58) Field of Search ..................................... 510/392, 530, 510/226, 320, 321, 382, 383, 319, 337, 339, 500, 498

(56) References Cited

U.S. PATENT DOCUMENTS

| B 458,819 | 4/1976 | Weber | 252/545 |
|---|---|---|---|
| 5,604,190 * | 2/1997 | Chowhan et al. | 510/114 |
| 5,820,696 * | 10/1998 | Kimura et al. | 134/42 |
| 5,939,369 * | 8/1999 | Chowhan et al. | 510/114 |

FOREIGN PATENT DOCUMENTS

| 0 508 381 | * 10/1992 | (EP) . |
|---|---|---|
| 0 757 095 | * 2/1997 | (EP) . |
| 0 957 157 | * 11/1999 | (EP) . |
| 0 958 836 | * 11/1999 | (EP) . |
| 1 354 761 | 5/1974 | (GB) . |
| 48 049984 | 7/1973 | (JP) . |
| WO96/06910 | 3/1996 | (WO) . |

OTHER PUBLICATIONS

Database WPI, Class A97, AN73–62619U, XP002077577.

* cited by examiner

*Primary Examiner*—Kery Fries
(74) *Attorney, Agent, or Firm*—Wayne C. Jaeschke; Glenn E. J. Murphy

(57) ABSTRACT

A stabilized liquid enzyme preparation containing a cleaning-active enzyme, a solvent selected from the group consisting of ethylene glycol, propylene glycol, glycerol, and mixtures thereof, and a stabilizer comprising a basic nitrogen compound selected from the group consisting of N,N-bis-(3-aminopropyl)-dodecyl amine, a salt of N,N-bis-(3-aminopropyl)-dodecyl amine, and mixtures thereof. Also, a method of cleaning an article by diluting the stabilized liquid enzyme preparation with water in a weight ratio of enzyme preparation to water of 1:500 to 1:5000 to form a cleaning solution, adding to the cleaning solution 0.01% to 0.2% by weight, based on the weight of cleaning solution, of a buffer concentrate to adjust the pH of the cleaning solution to 7 to 10; and contacting the article with a portion of the cleaning solution to effect cleaning thereof.

16 Claims, No Drawings

LIQUID ENZYME PREPARATION AND THE USE THEREOF

BACKGROUND OF THE INVENTION

This invention relates generally to the enzymatic cleaning of hard surfaces and, more particularly to a liquid stabilized enzyme preparation and to its use for cleaning hard surfaces, above all in dairies/creameries.

Deposits containing proteins and fats are formed on surfaces of containers and pipes which come into contact with milk or milk products in the production and processing of milk. Such deposits, which are extremely difficult to remove, occur to a particularly marked extent in milking machines, milk collection trucks, tanks, pipelines and heaters. On account of the obstinate nature of the soils, equipment of the type in question is generally cleaned with strongly alkaline and, in some cases, also strongly acidic cleaners which have to handled with great care on account of their highly corrosive properties. In addition, where cleaners of this type are used on sensitive materials, they can be expected to cause corrosion unless special precautionary measures are taken. Before they discharged into the main drainage system, the cleaners have to be neutralized.

On account of the difficulties involved in using highly alkaline or strongly acidic cleaning solutions, there has been no shortage of attempts to develop cleaning solutions which clean as effectively as the strongly alkaline or highly acidic cleaners despite a substantially neutral pH value. Above all, it has been proposed to use enzymes, especially proteases, for this purpose. Numerous publications on this subject have appeared in the literature (cf. for example International patent application WO 96/6910 where more literature references can be found). Although in principle adequate cleaning is possible, even at a neutral pH, where proteases are used, the use of these enzymes is attended by other difficulties. Thus, liquid concentrates are preferably used for preparing the actual cleaning solution, especially in institutional cleaning. Unfortunately, liquid enzyme concentrates quickly lose their effectiveness in storage because the enzymes present are denatured or otherwise lose their activity. For this reason, numerous attempts have been made to improve the stability of liquid enzyme preparations in storage by the addition of so-called stabilizers. For example, the addition of boric acid or borates and soluble potassium salts and even the addition of polyhydric alcohols are widely practised. Unfortunately, these stabilizers still do not provide a totally satisfactory solution to the problem.

The problem addressed by the present invention also was to improve the stability of liquid enzyme preparations. Another problem addressed by the invention was to develop enzyme preparations which would be suitable for cleaning hard surfaces, especially in the dairy industry. In addition, these enzyme preparations would be suitable for the preparation of reusable cleaning solutions, above all of the type required for institutional cleaning.

It has surprisingly been found that the problems stated above can be solved by the addition of certain basic nitrogen compounds to the liquid enzyme preparations.

DESCRIPTION OF THE INVENTION

Accordingly, the present invention relates to a liquid stabilized enzyme preparation which contains a protease, a solvent from the group consisting of ethylene glycol, propylene glycol, glycerol and mixtures thereof and a stabilizer from the group consisting of polyhexamethylene biguanide, N,N-bis-(3-aminopropyl)-dodecyl amine, salts thereof and mixtures of these compounds. In a preferred embodiment, the enzyme preparation additionally contains water and optionally other auxiliaries, more especially from the group of surfactants, solubilizers and mixtures thereof. The present invention also relates to the use of the enzyme preparation for the preparation of a cleaning solution for cleaning dairy equipment and to a process for cleaning dairy equipment using such cleaning solutions in the substantially neutral to weakly alkaline range.

The basic nitrogen compounds used to stabilize the liquid enzyme preparation are substances which, hitherto, have been used almost exclusively in disinfectants by virtue of their antimicrobial activity. Thus, polyhexamethylene biguanide hydrochloride is available for this purpose under the names of Lonzabac BFG and Vantocil IB from Lonza and Zeneca Biocides, respectively. N,N-bis-(3-aminopropyl)-dodecyl amine is available for this purpose under the name of Lonzabac-12.30 or Bardac 21from Lonza AG. The fact that these antimicrobial agents have a stabilizing effect on liquid enzyme preparations was not known. One particular advantage is that even very small quantities of these basic nitrogen compounds are sufficient to stabilize the liquid enzyme preparation. They are preferably used in quantities of about 0.5 to about 5% by weight and more preferably in quantities of about 1 to about 3% by weight, based on the liquid enzyme preparation as a whole, although it may even be appropriate in special cases to use the stabilizers in quantities outside these concentration ranges. The above-mentioned commercial forms of the two stabilizers, i.e. as the hydrochloride or free base, are the forms in which they are preferably used although it is of course also possible to use other salts of the basic nitrogen compounds should this appear appropriate in any particular case. Apart from the basic nitrogen compounds themselves, any salts with inorganic or organic acids which are soluble in the enzyme preparation may also be used.

The liquid enzyme preparations contain as solvent at least one substance from the group consisting of ethylene glycol, propylene glycol and glycerol. These solvents may be used on their own although they are preferably used together with water as an additional solvent. The content of solvents from the group consisting of ethylene glycol, propylene glycol, glycerol and mixtures thereof in the enzyme preparations is preferably from about 10 to about 70% by weight and more preferably from about 30 to about 50% weight, based on the preparation as a whole. If water is used as an additional solvent, its content is preferably from about 5 to about 40% by weight and more preferably from about 10 to about 30% by weight, again based on the liquid enzyme preparation as a whole. Since potassium salts generally have a stabilizing effect on enzyme solutions, tap water is preferably used for the enzyme preparations.

Although the stabilizing effect of the nitrogen-containing bases mentioned above extends to liquid preparations of any enzymes, it is preferably used in accordance with the invention for stabilizing solutions of cleaning-active enzymes, i.e. for enzymes which are of use in some way or other in the cleaning of hard surfaces or textiles. Accordingly, the enzyme preparations stabilized in accordance with the invention preferably contain at least one enzyme from the group of proteases (peptidases), amylases, cellulases, glycosidases, lipases and oxidoreductases. The preparations according to the invention may also contain several enzymes from various classes providing no troublesome interactions between the enzymes occur. For the particularly preferred application of the preparations according to the invention, i.e. the cleaning of hard surfaces in the processing of milk, the preparations contain at least one protease, more particularly a protease on its own or in the form of a mixture with other proteases.

The quantity of enzyme in the preparations according to the invention is selected according to the purpose for which the preparations are intended. Accordingly, the quantity of enzymes can be freely selected within very wide limits. The advantageous stabilizing effect of the basic nitrogen compounds occurs at all enzyme concentrations. The enzyme concentration in the preparations is of course also dependent upon the specific activity of the particular enzyme used. Accordingly, where quantities are mentioned in the following for the enzymes, they should be regarded only as rough guides which may be exceeded in either direction as required. The concentration figures apply to pure enzyme and do not include the diluents, auxiliaries and solvents frequently added to the enzyme preparations by manufacturers. On the other hand, the enzyme preparations according to the invention are normally prepared from the enzyme concentrates marketed by manufacturers, so that the auxiliaries and diluents automatically become components of the preparations according to the invention. The preparation according to the invention is preferably prepared from highly concentrated liquid enzyme preparations which are marketed by various manufacturers. For example, liquid proteases are obtainable under the names of Alkalase, Savinase, Purafect and Maxatase from such manufacturers as Genencor and Novo. Preferred enzymes are those which develop their optimal effect in the vicinity of the pH value at which the enzyme preparations are used for cleaning. The enzyme preparations according to the invention preferably contain about 1to about 15% by weight and, more preferably, about 2 to about 8% by weight of cleaning-active enzyme. In the case of proteases, this should preferably correspond to between about 5 and about 100 Anson units per 100 g of preparation.

Besides the components already mentioned, the enzyme preparations according to the invention may contain other auxiliaries if this is appropriate for the particular application. Such auxiliaries are, above all, surfactants for boosting the cleaning effect and, in the case of water-containing preparations, solubilizers (hydrotropes). Examples of further auxiliaries and additives are other typical enzyme stabilizers, such as soluble potassium salts and borates, thickeners, dyes, antioxidants, foam inhibitors, preservatives and buffers. When choosing auxiliaries and additives, it is important to ensure that no troublesome interactions with the other components of the preparations according to the invention occur. Thus, in principle, surfactants from any known classes may be used although nonionic, cationic and amphoteric surfactants are particularly preferred, nonionic surfactants being the most important.

Suitable nonionic surfactants are, in particular, the addition products of long-chain alcohols, alkylphenols and amides and carboxylic acids with ethylene oxide (EO), optionally together with propylene oxide (PO). These include, for example, the addition products of long-chain primary or secondary alcohols containing 12 to 18 carbon atoms in the chain, more especially fatty alcohols and oxoalcohols with the same chain length, and the addition products of ethylene oxide and fatty acids containing 12 to 18 carbon atoms in the chain with, preferably, 2 to 6 mol of ethylene oxide. The mixed addition products of ethylene and propylene oxide with fatty alcohols containing 12 to 18 carbon atoms, especially those containing about 2 mol of EO and about 4 mol of PO in the molecule, are particularly preferred. Examples of suitable nonionic surfactants are the fatty alcohol alkoxylates marketed by Henkel KGaA under the names of Dehypon®LS24, Dehypon® LS54, Eumulgin® 05, Dehydol® LT8, Dehydol® LT6 and Dehydol® LS6.

Other suitable nonionic surfactants are the esters of fatty acids containing 6 to 12 carbon atoms and polyols, more especially carbohydrates, for example glucose. If nonionic surfactants are present in the enzyme preparations according to the invention, their percentage content is preferably from about 5 to about 50% by weight and more preferably from about 20 to about 40% by weight, based on the preparation as a whole.

Suitable cationic surfactants are, in particular, aliphatic or hetero-cyclic quaternary ammonium compounds and quaternary phosphonium compounds which have at least one long-chain $C_{8-18}$ alkyl group at the quaternary center. Examples of such cationic surfactants are cocoalkyl benzyl dimethyl ammonium chloride, dioctyl dimethyl ammonium chloride and tributyl tetradecyl phosphonium chloride.

Suitable amphoteric surfactants are, in particular, $C_{8-18}$ fatty acid amide derivatives of betaine structure, more especially derivatives of glycine, for example cocoalkyl dimethyl ammonium betaine.

Examples of suitable solubilizers are cumene sulfonate, xylene sulfonate and octyl sulfonate, although other typical solubilizers may of course also be used. The solubilizer content is selected according to requirements and is preferably from about 1 to about 10% by weight and more preferably from about 2 to about 5% by weight, based on the preparation as a whole.

The enzyme preparations according to the invention are normally not used as such for cleaning, but instead form the starting material for the preparation of the actual cleaning solution. In the most simple case, the cleaning solution is prepared by diluting the enzyme preparation with water although, in many cases, other components are added to the cleaning solution. In the preferred use of the enzyme preparation for cleaning dairy equipment, the enzyme preparations are diluted with water, preferably in a ratio of about 1:5000 to 1:500 and more preferably in a ratio of 1:3000 to 1:1000. In one particularly preferred embodiment, other cleaning-active substances, more especially from the group of complexing agents, alkalis and surfactants, are added to the cleaning solution for this purpose. It is of course also possible to add other auxiliaries at this point, for example foam inhibitors and buffers, such as soluble carbonates or silicates.

In one particular cleaning process for dairy equipment, to which the present invention also relates, the cleaning solution is prepared by diluting an enzyme preparation according to the invention with water in the ratio mentioned above and adding a buffer concentrate. This buffer concentrate is used in a quantity of about 0.01 to about 0.2% by weight and preferably in a quantity of about 0.03 to 0.1% by weight, based on the dilute cleaning solution as a whole, with a view to adjusting the cleaning solution to a pH value of about 8 to about to about 10 and preferably in the range from about 8 to about 9.5. Depending on the starting pH value of the enzyme preparation, this buffer concentrate may contain acidic or alkaline substances, for example citric acid, sodium carbonate or sodium hydrogen carbonate.

A buffer concentrate particularly preferred for adjusting an alkaline pH value has the following composition:

3 to 20% by weight and preferably 5 to 10% by weight of complexing agent from the group of polyphosphates, poly-acrylates and mixtures thereof, 3 to 20% by weight and preferably 5 to 10% by weight of alkali metal hydroxide from the group consisting of sodium hydroxide, potassium hydroxide and mixtures thereof, 5 to 30% by weight and preferably 10 to 20% by weight of alkali metal carbonate from the group consisting of sodium carbonate, potassium carbonate and mixtures thereof and 20 to 80% by weight and preferably 40 to 60% by weight of water.

The cleaning of dairy equipment with the cleaning solution prepared in this way may be carried out by hand, although it is preferably carried out to a greater or lesser extent by machine. The equipment is normally first prerinsed with optionally preheated water before it is actually cleaned with the cleaning solution prepared in accordance with the invention. Cleaning may be carried at room temperature, but is preferably carried out at elevated temperatures, more particularly at temperatures of up to about 70° C., above all in the case of machine cleaning. Temperatures of about 40 to about 60° C. are particularly preferred, temperatures of about 50 to about 60° C. being most particularly preferred. Cleaning may be mechanically assisted, although agitation of the cleaning solution is sufficient for satisfactory cleaning, above all at relatively high temperatures. In the case of closed systems, the cleaning solution is pump-circulated and optionally distributed over the surfaces to be cleaned, for example inside tanks, by spray heads or similar devices. The cleaning solution is circulated for a sufficient time, for example for about 5 to about 30 minutes, until the required degree of cleanness is achieved. This cleaning process is also known as cleaning-in-place (CIP). After the cleaning solution has been pumped off, the equipment is normally rinsed with fresh water and, if necessary, is even treated with a disinfecting solution after removal of the fresh water and then rerinsed with fresh water.

In one particularly advantageous embodiment, the cleaning solutions prepared with the enzyme preparation according to the invention do not undergo microbial infestation by virtue of the presence of the microbicidally active basic nitrogen compounds and, accordingly, can be stored for further cleaning tasks. To this end, they are stored in storage tanks and are only augmented by the quantity of solution which remains in the equipment during cleaning and which is lost with the rinsing water. Since, in this way, only a few percent of the cleaning solution enters the wastewater during each cleaning operation, the pollution level of the wastewater is extremely low by comparison with conventional processes where the entire cleaning solution has to be discarded after each cleaning operation. Compared with the reusable highly alkaline cleaners, the absence of phosphate in the cleaning solution and the low degree of corrosion may be regarded as advantages.

EXAMPLES

1. Stabilized liquid enzyme preparations

Three liquid enzyme preparations 1, 2 and 3 were prepared by mixing the individual components. Preparations 2 and 3 correspond to the invention whereas preparation 1 does not contain a stabilizing nitrogen compound. The contents of individual components are shown in % by weight in Table 1 for the three preparations.

In order to determine their stability in storage, the preparations were subjected to a rigorous storage test at 60° C. To this end, the preparations were stored in closed glass vessels in a heating cabinet. After 20, 40 and 60 minutes, samples were taken to determine the enzyme content by a standard method. The results are also set out in Table 1 in the form of percentages based on a starting value of 100%. The stabilizing effect of the nitrogen-containing compounds can clearly be seen.

TABLE 1

| Components | 1 | 2 | 3 |
|---|---|---|---|
| Tap water, 16° German hardness | 20 | 28 | 28 |
| 1,2-Propylene glycol | 36 | 36 | 36 |
| $C_{12\text{-}18}$ Fatty alcohol + 6 EO | 2 | 2 | 2 |
| $C_{12\text{-}14}$ Fatty alcohol + 5 EO + 4 PO | 23 | 23 | 23 |
| Na cumene sulfonate (40%) | 5 | 5 | 5 |
| Protease (Savinase, a product of Novo) | 5 | 5 | 5 |
| Lonzabac 1230 = bis-(3-aminopropyl)-dodecylamine | — | 1 | — |
| Vantocil IB = Polyhexamethylene bisbiguanide HCl | — | — | 1 |
| Residual enzyme activity in % of the starting value after storage at 60° C. | | | |
| After 20 minutes | 76 | 72 | 92 |
| After 40 minutes | 48 | 63 | 73 |
| After 60 minutes | 37 | 53 | 58 |

2. Cleaning effect of the enzymatic cleaning solutions

The cleaning effect was tested on artificially soiled stainless steel plates by comparison with a conventional highly alkaline cleaner. The standard soil was prepared as follows:

Stainless steel plates measuring 5×10 cm were wetted with 0.25 g of condensed milk (fat content 10%) and then dried. The stainless steel plates thus soiled were immersed 10 times in the cleaning solution (2000 ml) heated to 50° C. by a lifting mechanism and then rinsed with distilled water and dried. The cleaning effect was gravimetrically determined by calculating the quantity of soil removed from the weight of the untreated stainless steel plates, the soiled stainless steel plates and the cleaned stainless steel plates.

A concentrated cleaner (concentrate) with the following composition was used for comparison:

35% by weight of sodium hypochloride solution (12%)

15% by weight of caustic soda (50%)

5% by weight of $K_5P_3O_{10}$

40% by weight of distilled water

To prepare the cleaning solution, the concentrate was diluted with tap water in a ratio of 1:100. The cleaning solution had a pH value of 12.3.

A liquid enzyme preparation with the following composition was tested as the preparation according to the invention:

10% by weight of liquid protease preparation (Savinase 16.0 LEX, a Novo product)

40% by weight of 1,2 propylene glycol

20% by weight of $C_{12\text{-}14}$ fatty alcohol +4EO+5PO

5% by weight of polyhexamethylene biguanide hydrochloride

25% by weight of water

To prepare the cleaning solution, this preparation was diluted with water in a ratio of 1:1000. The pH value of the dilute solution was adjusted to 8.5 by addition of potassium carbonate.

A cleaning effect of 99.3% at 50° C. was achieved with the conventional cleaner in the form of the 1% solution. By contrast, a cleaning effect of 99.9% at 50° C. was achieved with an only 0.1% solution of the enzyme preparation according to the invention.

3. Bacterial growth in the cleaning solution

In order to determine whether the dilute cleaning solutions obtained from the enzyme preparations according to the invention have long-term resistance to microbiological infestation and can therefore be stored, the solutions were inoculated with a germ mixture and the germ content was determined after storage for 21 days at 25° C. The composition of the preparations from which the cleaning solutions were prepared by dilution with water in a ratio of 1:2000 are shown in % by weight in Table 2. 0.75% by weight of untreated milk was added to the cleaning solutions in order to simulate the organic challenge. 1 ml of a bacterial and fungal cocktail containing the following germs was then added per liter of cleaning solution:

| Bacterial cocktail ($3 \times 10^8$/ml) of: | |
|---|---|
| Staphylococcus aureus | ATCC 6538 |
| Enerococcus faecium | ATCC 6057 |
| Escherichia coli | ATCC 11229 |
| Pseudomonas aeruginosa | ATCC 15442 |
| Enterobacter aerogenes | DSM 30053 |
| Fungal cocktail ($15 \times 10^7$ml) of: | |
| Candida albicans | ATCC 10231 |
| Aspergillus niger | ATCC 6275 |
| Penicilium rubrum | CMI 113729 |
| Trichoderma viride | BAM T 21 |

The germ count after storage (per ml of cleaning solution) is also shown in Table 2. The germ-inhibiting effect in the cleaning solutions (of 5 and 6) prepared in accordance with the invention can clearly be seen.

TABLE 2

| Components | 4 | 5 | 6 |
|---|---|---|---|
| H$_2$O, distilled | 27 | 26 | 26 |
| 1,2-Propylene glycol | 36 | 36 | 36 |
| C$_{12-18}$ Fatty alcohol + 6 EO | 6 | 6 | 6 |
| C$_{12-14}$ Fatty alcohol + 5 EO + 4 PO | 20 | 20 | 20 |
| Na Cumene sulfonate (40%) | 5 | 5 | 5 |
| Protease (Savinase 16.0 LEX, a product of Novo) | 6 | 6 | 6 |
| Vantocil IB = polyhexamethylene bisbiguanide HCl | — | 1 | — |
| Lonzabac 1230 = bis-(3-aminopropyl)-dodecylamine | — | — | — |
| Germ count after 21 days | $10^7$ | $10^2$ | $10^1$ to $10^7$ |

What is claimed is:

1. A stabilized liquid enzyme preparation comprising a cleaning-active enzyme, a solvent selected from the group consisting of ethylene glycol, proplyene glycol, glycerol and mixtures thereof, and a stabilizer comprising a basic nitrogen compound selected from the group consisting of N,N-bis-(3-aminopropyl)-dodecyl amine, a salt of N,N-bis-(3-aminopropyl)-dodecyl amine, and mixtures thereof.

2. The stabilized liquid enzyme preparation of claim 1, wherein the enzyme is selected from the group consisting of proteases, lipases, amylases, and mixtures thereof.

3. The stabilized liquid enzyme preparation of claim 2, wherein the enzyme is at least one protease.

4. The stabilized liquid enzyme preparation of claim 1, further comprising at least one auxiliary selected from the group consisting of surfactants, solubilizers, and mixtures thereof.

5. The stabilized liquid enzyme preparation of claim 4, wherein the surfactant comprises an addition product of ethylene oxide and optionally propylene oxide with a C$_{12}$ to C$_{18}$ alcohol.

6. The stabilized liquid enzyme preparation of claim 1, comprising 10% to 70% by weight of the solvent, 0.5% to 5% by weight of the stabilizer, and 1% to 15% by weight of the enzyme.

7. The stabilized liquid enzyme preparation of claim 6, comprising 30% to 50% by weight of the solvent, 1% to 3% by weight of the stabilizer, and 2% to 8% by weight of the enzyme.

8. The stabilized liquid enzyme preparation of claim 6, comprising 10% to 80% by weight of water.

9. The stabilized liquid enzyme preparation of claim 6, comprising 5% to 40% by weight of water.

10. The stabilized liquid enzyme preparation of claim 6, further comprising 5% to 50% by weight of a water.

11. The stabilized liquid enzyme preparation of claim 6, comprising 10% to 30% by weight of a surfactant comprising an addition product of ethylene oxide and optionally propylene oxide with a fatty alcohol.

12. The stabilized liquid enzyme preparation of claim 11, comprising 20% to 40% by weight of a surfactant comprising an addition product of ethylene oxide and optionally propylene oxide with a fatty alcohol.

13. A process of cleaning an article in need thereof comprising the steps of:
   a. diluting a stabilized liquid enzyme prepration comprising a cleaning-active enzyme, a solvent selected from the group consisting of ethylene glycol, propylene glycol, glycerol, and mixtures thereof, and a stabilizer comprising a basic nitrogen compound selected from the group consisting of polyhexamethylene biguanide, a salt of polyhexamethylene biguanide, N,N-bis-(3-aminopropyl)-dodecyl amine, a salt of N,N-bis-(3-aminopropyl)-dodecyl amine, and mixtures thereof with water in a weight ratio of enzyme preparation to water of 1:500 to 1:5000 to form a cleaning solution;
   b. adding to the cleaning solution 0.01to 0.2% by weight, based on the weight of cleaning solution, of a buffer concentrate, wherein the buffer concentrate comprises 3% to 20% by weight or a complexing agent selected from the group consisting of polyphosphates, polyacrylates, and mixture thereof, 3% to 20% by weight of an alkali metal hydroxide selected from the group consisting of sodium hydroxide, potassium hydroxied, and mixtures thereof,5% to 30% by weight of an alkali metal carbonate selected from the group consisting of sodium carbonate, potassium carbonate, and mixtures thereof, and 20% to 80% by weight water, to adjust the pH of the cleaning solution to 7 to 10; and
   c. contacting the article with a portion of the cleaning solution to effect cleaning thereof.

14. The process of claim 13, wherein the weight ratio of enzyme preparation to water is 1:1000 to 1:3000.

15. The process of claim 13, wherein 0.03% to 0.1% by weight, based on the weight of cleaning solution, of buffer concentrate are added to the cleaning solution.

16. The process of claim 13, wherein the buffer concentrate comprises 5% to 10% by weight of the complexing agent, 5% to 10% by weight of the alkali metal hydroxide, 10% to 20% by weight of the alkali metal carbonate, and 40% to 60% by weight of water.

* * * * *